(12) United States Patent
Nelson

(10) Patent No.: US 8,518,096 B2
(45) Date of Patent: Aug. 27, 2013

(54) ELEPHANT TRUNK THORACIC ENDOGRAFT AND DELIVERY SYSTEM

(75) Inventor: Kristoff Nelson, Boston, MA (US)

(73) Assignee: Lifeshield Sciences LLC, Plano, TX (US)

( * ) Notice: Subject to any disclaimer, the term of this patent is extended or adjusted under 35 U.S.C. 154(b) by 710 days.

(21) Appl. No.: 10/234,070

(22) Filed: Sep. 3, 2002

(65) Prior Publication Data
US 2004/0044395 A1    Mar. 4, 2004

(51) Int. Cl.
*A61F 2/06* (2006.01)

(52) U.S. Cl.
USPC .......................... 623/1.11; 623/1.12

(58) Field of Classification Search
CPC ........................................ A61F 2/06
USPC .................. 623/1.11, 1.12, 1.13; 606/191, 606/195
See application file for complete search history.

(56) References Cited

U.S. PATENT DOCUMENTS

| | | | |
|---|---|---|---|
| 5,108,416 A * | 4/1992 | Ryan et al. | 606/194 |
| 5,201,757 A | 4/1993 | Heyn et al. | |
| 5,383,928 A | 1/1995 | Scott et al. | |
| 5,415,664 A | 5/1995 | Pinchuk | |
| 5,480,423 A * | 1/1996 | Ravenscroft et al. | 623/1.11 |
| 5,578,071 A | 11/1996 | Parodi | |
| 5,591,229 A | 1/1997 | Parodi | |
| 5,662,703 A | 9/1997 | Yurek et al. | |
| 5,769,887 A * | 6/1998 | Brown et al. | 623/1.23 |
| 5,948,017 A * | 9/1999 | Taheri | 623/1.14 |
| 5,954,764 A | 9/1999 | Parodi | |
| 5,984,964 A * | 11/1999 | Roberts et al. | 623/1.11 |
| 5,989,280 A | 11/1999 | Euteneuer et al. | |
| 6,004,347 A * | 12/1999 | McNamara et al. | 623/23.64 |
| 6,123,723 A | 9/2000 | Konya et al. | |
| 6,126,685 A * | 10/2000 | Lenker et al. | 623/1.11 |
| 6,162,246 A | 12/2000 | Barone | |
| 6,371,979 B1 * | 4/2002 | Beyar et al. | 623/1.12 |
| 6,562,063 B1 | 5/2003 | Euteneuer et al. | |
| 2001/0053929 A1 | 12/2001 | Vonesh et al. | |
| 2002/0029046 A1 | 3/2002 | Lorentzen Cornelius et al. | |
| 2002/0038142 A1 | 3/2002 | Khosravi et al. | |
| 2002/0120322 A1 | 8/2002 | Thompson et al. | |

FOREIGN PATENT DOCUMENTS

| | | |
|---|---|---|
| FR | 2 756 173 A1 | 11/1996 |
| JP | 08-173548 * | 7/1996 |
| WO | 9853761 A1 | 12/1998 |

OTHER PUBLICATIONS

International Search Report issued in International Application No. PCT/US03/15121 filed Mar. 9, 2002.

* cited by examiner

*Primary Examiner* — Thomas J Sweet
*Assistant Examiner* — Christopher D Prone
(74) *Attorney, Agent, or Firm* — Vidas, Arrett & Steinkraus, P.A.

(57) ABSTRACT

A delivery system for delivering a device within a body lumen. The delivery system includes a self-expanding stent/graft composite prosthesis and a deployment device. The deployment device includes an outer sheath which overlies the graft, and a stent retaining means for maintaining the one end of the stent in a radially compressed state. The outer sheath is retractable with respect to the graft, and the stent retaining means is removable to allow the stent end to radially expand. The deployment device may further include an inner sheath to overlie the composite and is retractable with respect to the composite. An endoluminal prosthesis including a graft attached to one stent and a second stent unattached within the graft lumen.

14 Claims, 5 Drawing Sheets

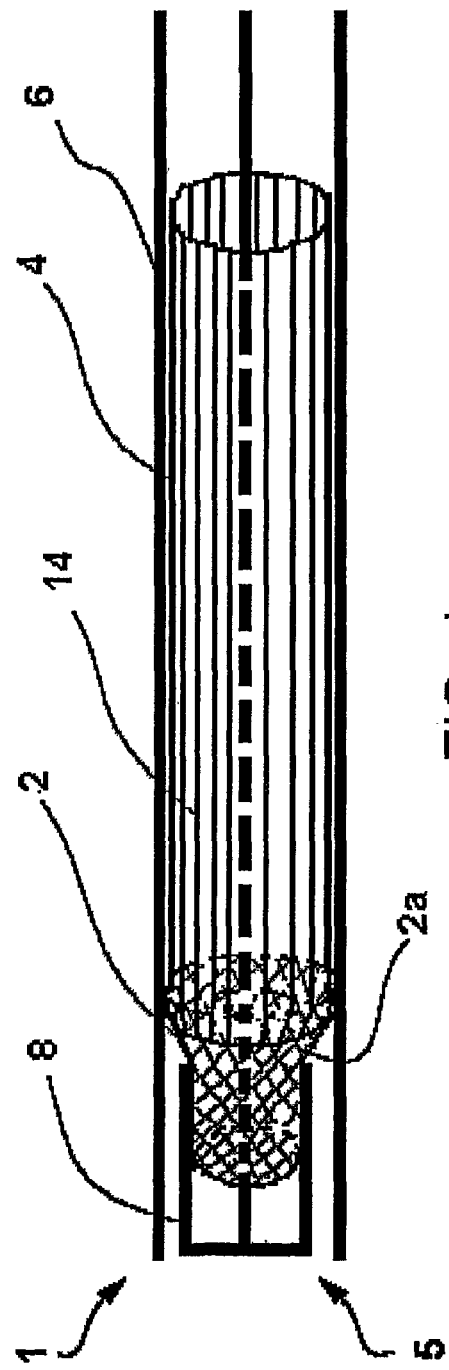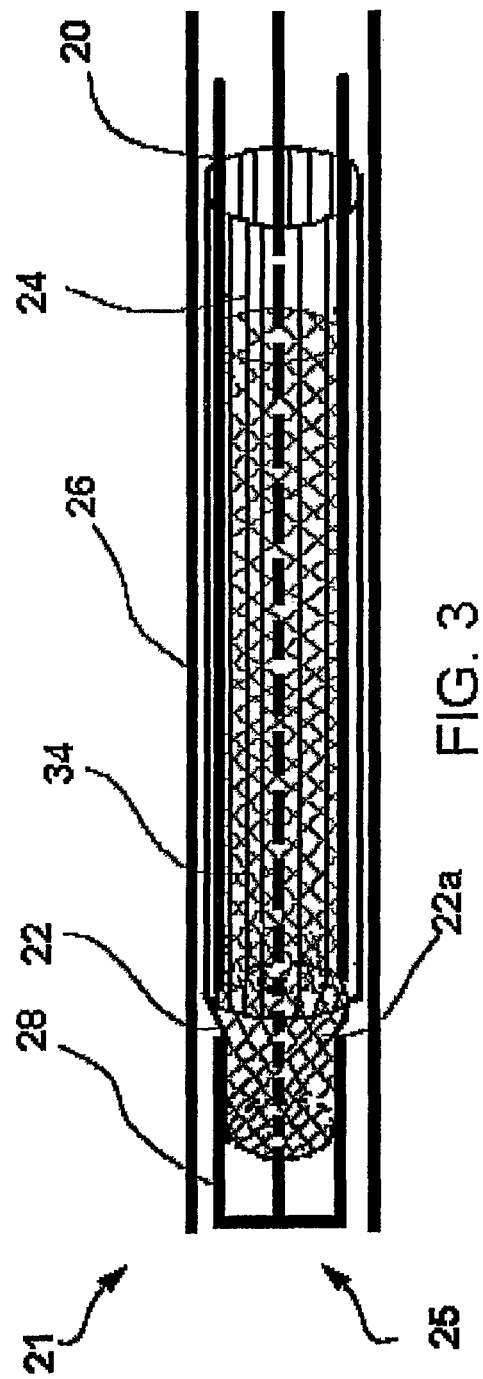

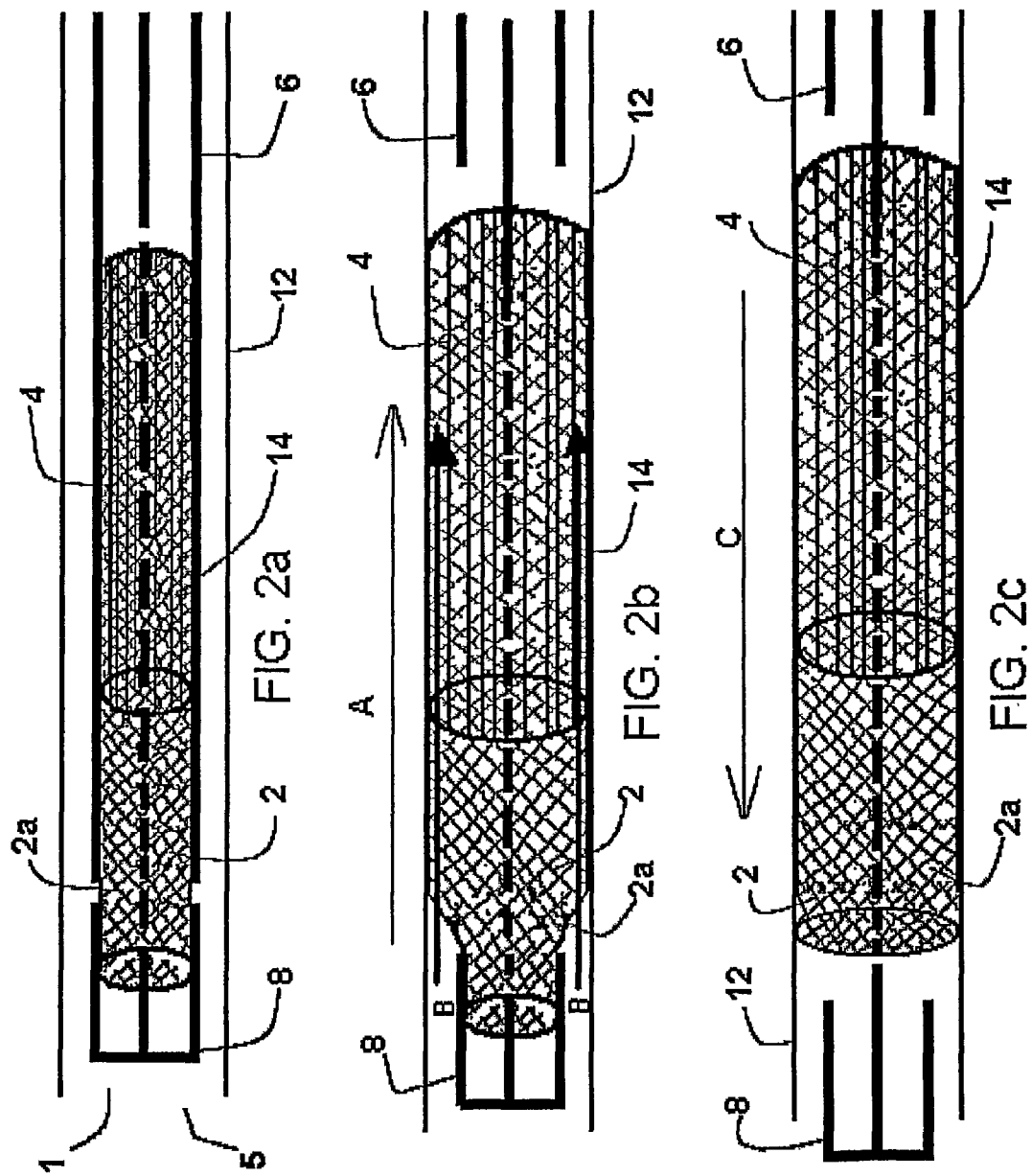

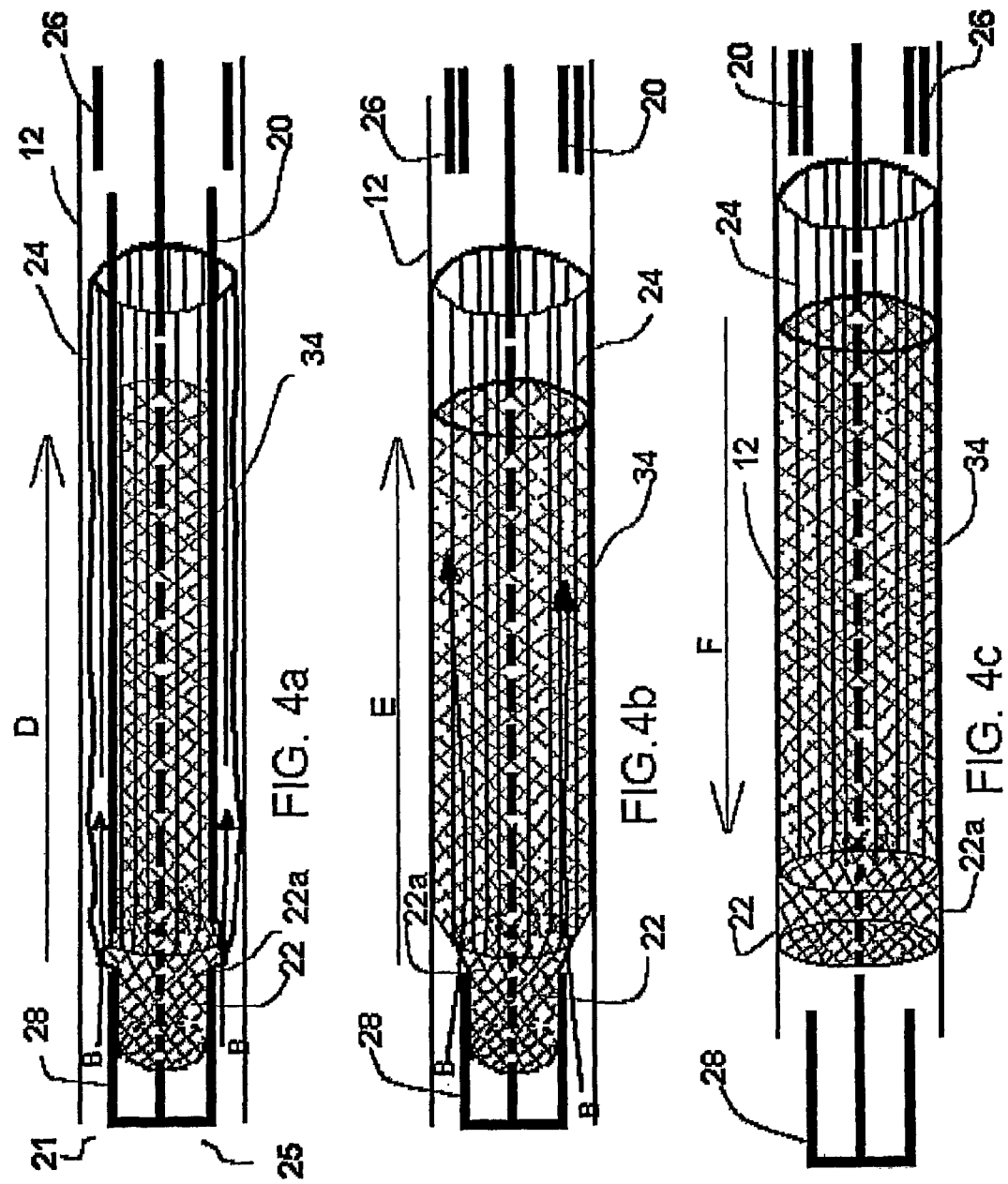

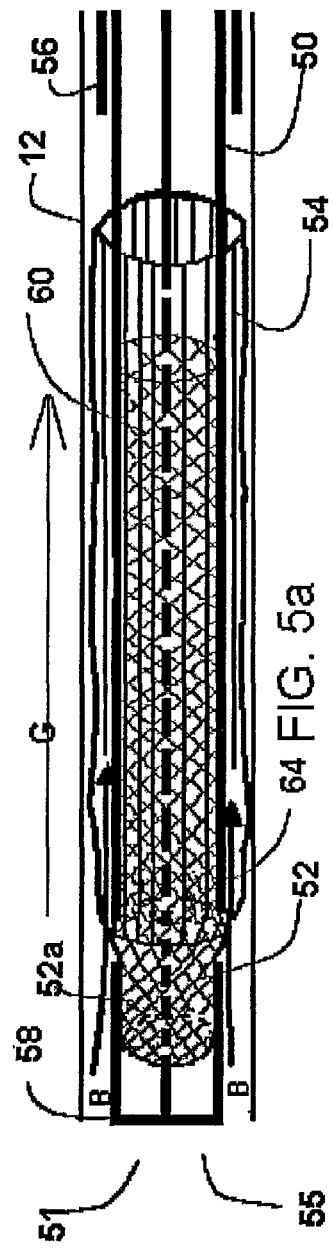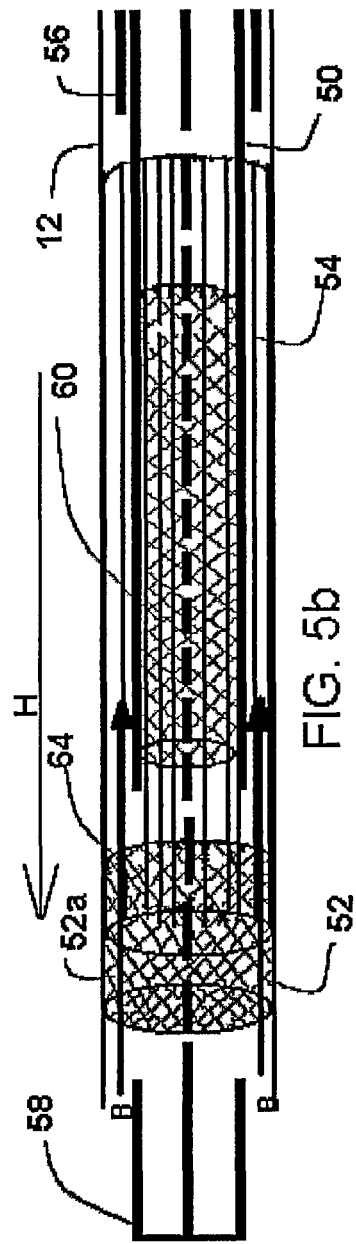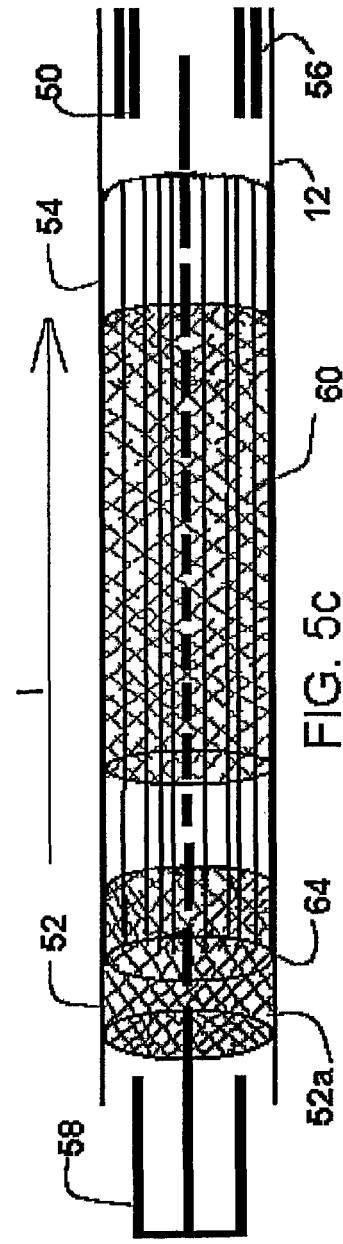

ELEPHANT TRUNK THORACIC ENDOGRAFT AND DELIVERY SYSTEM

FIELD OF THE INVENTION

The present invention relates generally to a endoluminal prosthesis and a delivery system for deploying an endoluminal prosthesis within a body lumen. More particularly, the present invention provides a delivery device retaining an endoluminal prosthesis during delivery and additionally for the deployment of the endoluminal prosthesis at a target site within the lumen.

BACKGROUND OF THE INVENTION

Endoluminal prostheses are typically used to repair, replace, or otherwise correct a diseased or damaged blood vessel. An artery or vein may be diseased in a variety of ways. The prosthesis may therefore be used to prevent or treat a wide variety of defects such as stenosis of the vessel, thrombosis, occlusion, or an aneurysm and dissections.

One type of endoluminal prosthesis used in treatment and repair of diseases in various blood vessels is a stent. A stent is a generally longitudinal tubular device which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of materials, including textile and non-textile materials. Grafts also generally have an unexpanded insertion diameter and an expanded implantation diameter which is greater than the unexpanded diameter. The graft is sutured to the lumen to secure it in place.

It is also known to use both a stent and a graft to provide additional support for blood flow through weakened sections of a blood vessel. In endovascular applications the use of a stent and a graft in combination is becoming increasingly important because the combination not only effectively allows the passage of blood therethrough, but also ensures the implant will remain open. The use of a both a stent and a graft is available in various forms, such as a stent/graft composite or a multi-stage stent/graft where the stent secures the graft in place by pinning it between the stent and the vascular wall. Such stent/graft composite prosthesis are described in U.S. Pat. No. 5,578,071 to Parodi, and U.S. Pat. No. 6,162,246 to Barone.

It is also known to provide delivery systems for delivering such prostheses intraluminally. These standard delivery systems generally include catheters with the prosthesis removably mounted to the distal end of the catheter. Quite often a catheter, introducer sheath, or other similar retaining means is disposed over the prosthesis to removably support the prosthesis on the catheter. Once the prosthesis is situated in the target site in the lumen, the catheter is removed by pulling the sheath or retaining means away from the prosthesis to allow the expansion.

The delivery systems for the multi-stage stent/grafts are more complex because the different expansion properties between the graft and the stent, and the frictional relationship between the two in the sheath. In certain situations irregular expansion of the graft may occur, provoking folds on the graft that act as constrictor rings to limit the expansion of the stent. Moreover, prosthesis employing self-expanding stents typically experience longitudinal lengthening when compressed inside the sheath. When liberated inside the vascular lumen, they radially expand and longitudinally reduce. This change in shape poses a problem when a graft covers the outside of the stent because the grafts tend to deform due to the force exerted on the graft by the moving stent. Therefore multiple deployment systems are used when delivering one then one stent or graft.

Procedural success of the deployment of the stent/graft and the function of the stent/graft require accuracy of deployment and ability to reposition. Accuracy is affected by the environment of deployment being a continuous blood-flow, the location of the procedure in the vascular system, and the design of the stent/graft prosthesis and deployment device. For example, pressure from the high volume of blood flow, especially in the thoracic aorta, must be overcome by the delivery device in order to locate the site of deployment and accurately set the stent/graft prosthesis. The location of deployment adds to the difficulty of placement if, for example, a stent/graft prosthesis is used as an interventional repair of a thoracic aortic aneurysm. A thoracic aortic aneurysm has the added complications of large amounts of blood flowing through this aorta, and the multiple outlet arteries disposing blood thereof. Procedural success requires deploying the stent/graft such that the proximal and distal sections of the device are sited in the healthier tissue. In a very diseased thoracic aorta where the aneurysm is up to the left subclavian or left common carotid, a stent/graft needs to anchor adjacent to or above the left subclavian. The placement is critical because the graft section must not cover the left subclavian to allow for blood flow to the left subclavian through the open cells of the stent. If the stent/graft prosthesis is deployed such that the graft section covers the left subclavian, then a blockage of the left subclavian would be formed by the graft. If the graft section is deployed too far downstream, then occlusion of the aneurysm may not be achieved.

The accuracy of the placement of the stent/graft prosthesis is critical. If the stent/graft prosthesis is deployed too low into the diseased section, there is the potential for rupturing the wall, and the aneurysm is not occluded by graft. Also, in certain instances the stent/graft prosthesis may not properly anchor and the prosthesis may pose a potential blockage problem. If the stent/graft prosthesis is anchored too high it may block or cut off other critical arteries.

The design of the stent/graft deployment device directly affects the performance and accuracy of the delivery device in the fluid flow environment. For example, the inability to reposition the stent/graft upon deployment, and difficulties associated with maneuvering the device within the arteries. The design also attributes to the amount of retrograde pressure experienced from the blood flow during deployment. This retrograde pressure caused by the obstruction of blood flow causes the graft to twist, crumble and not properly unfold, and the stent may not anchor properly, move or shift during or after deployment.

Thus, there is a need in the art for a deployment device that accurately deploys a prosthesis, eliminating problems associated with concurrent deployment of a stent and graft, and blood flow obstruction, retrograde pressure. There is a need for a delivery device that offers the flexibility of post-deployment adjustments, and is least obstructive to the blood flow upon deployment.

SUMMARY OF THE INVENTION

The present invention provides a stent-graft and method of delivery of a device within a body lumen. The system includes a stent/graft composite prosthesis and a deployment device. The stent/graft composite prosthesis includes a radially balloon expandable or self-expanding stent and an elongated graft secured to the stent. The deployment device includes an elongated outer sheath and a stent retaining means. The elongated outer sheath is overlying the graft and the outer sheath being retractable with respect to the graft. The stent retaining means for maintaining the end of the composite in a radially compressed state. The stent retaining means being removable from the end for allowing the radial expansion thereof to attach to the graft to the body lumen.

A further version of the delivery system of the present invention includes a deployment device including an outer sheath, inner sheath and a stent retaining means. The elongated outer sheath is for overlying the graft. The elongated inner sheath is for overlying the stent and is retractable with respect to the stent. The stent retaining means is for maintaining an end of the composite in a radially compressed state.

Yet another version of the delivery system of the present invention includes the deployment device including an elongated outer sheath, an inner sheath and a stent retaining means. The elongated outer sheath is for overlying the stent and is retractable with respect to the stent. The elongated inner sheath is for overlying the graft and is retractable with respect to the graft, and the stent retaining means is for maintaining an end to the composite in a radially compressed state. The retaining means is retractable from the end for allowing the radial expansion thereof to attach to the graft to the body lumen.

A further version of the delivery system of the present invention includes a stent/graft composite prosthesis and a deployment device. The stent/graft composite prosthesis comprising a first radially balloon expandable or self-expanding stent, an elongated graft secured to said first stent, and a second radially balloon expandable or self-expanding stent. The deployment device includes an elongated outer sheath, an elongated inner sheath and a stent retaining means. The elongated outer sheath is for overlying the graft. The outer sheath is retractable with respect to the graft. The elongated inner sheath is for overlying the second stent and is retractable with respect to the second stent. The stent retaining means is for maintaining an end of the composite in a radially compressed state. The retaining means is removable from the end for allowing said radial expansion thereof to attach said graft to said body lumen.

BRIEF DESCRIPTION OF THE DRAWINGS

FIG. 1 is a schematic illustration of the delivery system of the present invention, having an outer sheath.

FIGS. 2a, 2b, and 2c are schematic illustrations of the deployment device of FIG. 1, having an outer sheath deploying the stent/graft of the present invention.

FIG. 3 is a schematic illustration of the delivery system of the present invention, having an outer sheath and an inner sheath.

FIGS. 4a, 4b and 4c are schematic illustrations of the deployment device of FIG. 3, having outer and inner sheath deploying the stent/graft of the present invention.

FIGS. 5a, 5b and 5c are schematic illustrations of the deployment device of FIG. 3, having outer and inner sheaths deploying the stent/graft and a second stent of the present invention.

DETAILED DESCRIPTION OF THE INVENTION

Figure 6:
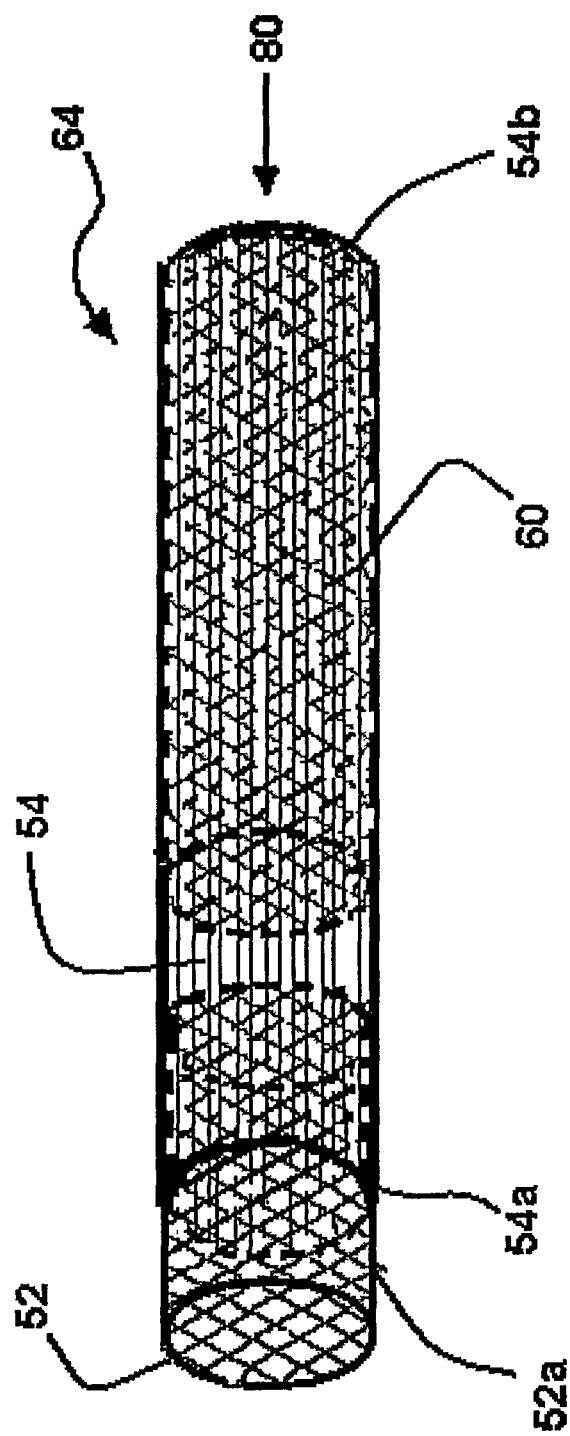
FIG. 6 is a schematic illustration of the endoluminal prosthesis of the present invention.

The present invention relates to an endoluminal prosthesis and a delivery system for delivering a device within a body lumen.

The present invention addresses the problems associated with prior stent/graft delivery system, such as: graft deformities like creases and folds; distal migration during stent deployment; retrograde pressure and reflux; and inaccurate placement and inability to readjust positioning.

The delivery system 1 of the present invention, as shown in FIG. 1 and FIGS. 2a-2c, include a stent/graft composite prosthesis 14 and a stent retaining device 5. The stent/graft composite prosthesis 14 is a generally tubular structure which includes a graft 4 and stent 2. The stent 2 is an elongated balloon expandable or self-expandable, tubular structure, with a pair of opposing ends and an open wall structure therebetween.

As is known in the art, the stent has two diameters, the compressed diameter and the expanded diameter wherein the compressed diameter is substantially smaller than the expanded diameter. The compressed diameter of the stent varies depending on the materials of construction and structure of the stent. In general, the compressed diameter must be small enough to allow for implantation through the vessel/lumen via a minimally invasive deployment system. The expanded diameter needs to be substantially the same diameter as the vessel/lumen in which it is to replace or repair. The expanded diameter needs to be large enough to allow the stent to sufficiently secure to the vessel/lumen wall without over expanding the vessel/lumen wall.

Various stent types and stent constructions may be employed in the invention. The stents may be capable of radially contracting, as well, and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of the stent may also be chosen from a host of geometries. For example, wire stents can be fastened into a continuous helical pattern, with or without a wavelike or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

As shown in FIG. 1 the stent 2 is longitudinally shorter than the attached graft 4, defining an extending stent portion 2a extending at one end beyond graft 4. While this embodiment is preferred, the stent length may vary in length with respect to the graft. For example, the stent can be the same length as the graft having the stent running continuously the length of the graft, or the stent may be longitudinally longer than the graft wherein the stent extends beyond the graft. The proximal end of the stent-graft composite must have an open architecture to allow blood passage during deployment (as in FIGS. 2b and 4b).

The graft 4 is an elongated compressible generally tubular structure with a pair of opposing ends and a graft wall therebetween. Any known graft material and structure may be used to form the graft of the present invention. The graft preferably has generally a tubular configuration. The graft may be made from a variety of well known materials, provided they have the requisite strength characteristics and biocompatibility properties. Examples of such materials are polyester, polypropylene, polyethylene, polytetrafluoroethylene, expanded polytetrafluoroethylene and polyurethane, DACRON, TEFLON (polytetrafluoroethylene), and TEFLON coated DACRON. The material can be extruded, knitted or woven, and can be warp or weft knitted. The graft can also be coated or impregnated with a bio-erodible, or degradable material, such as albumin, collagen, heparin or similar coating material. Additionally, the graft could have a coating of a biologically inert material, such as TEFLON. or porous polyurethane.

In general, the diameter of the graft varies depending on the use but generally should be substantially the same diameter as the inside diameter of the stent or vessel/lumen in which it is to replace or repair. The diameter should be large enough to allow for unobstructed blood flow and prevent retrograde pressure build-up in the blood flow. While cylindrical tubular configurations are shown, other tubular configurations may be employed.

The graft 4 extends circumferentially about the stent 2, and the graft 4 is securably attached to the stent 2. The attachment of the graft 4 to the stent 2 may be accomplished by mechanically securing or bonding the graft 4 to the stent 2. The attachment of the graft 4 to the stent 2 may be at one end of the stent 2 or anywhere between the two ends of the stent 2. Mechanical securement includes, but is not limited to, the use of sutures, anchoring barbs, textile cuffs and the like. Bonding includes, but is not limited to, chemical bonding, for instance, adhesive bonding, thermal bonding and the like.

As shown in FIG. 1 and FIGS. 2a-2c, the deployment device 5 of the present invention is designed for delivering and deploying the prosthesis 14. The device 5 includes an elongated outer sheath 6 which supports the prosthesis 14 in a compressed condition.

The delivery device 5 further adding a stent retaining member in the form of a nose cap 8, which supports extending portion 2a of stent 2 in compressed condition within outer sheath 6.

The outer sheath 6 is an elongated generally tubular structure which longitudinally surrounds the stent/graft composite 14. The outer sheath 6 has a diameter which is sufficiently small so as to be readily inserted within a body lumen 12 as shown in FIG. 4a. The outer sheath 6 can be made of a variety of biocompatible material such as metal, glass or polymeric material; such as nylon, polyurethane, polytetrafluoroethylene (PTFE), expanded polytetrafluoroethylene (ePTFE), fluorinated ethylene, propylene, polyimide, polyether ether ketone, and polybutylene terephthalate or any combination thereof. The outer sheath 6 can be a thin wall tube, extruded or a sheet formed into a tube.

The nose cap 8, which retains extended portion 2a of stent 2 may be formed of a brace or ring-like device that is removable to release the stent portion 2a and allow for expansion. The nose cap 8 is made from a material which is compatible with the body and small enough to be placed within a body lumen 12. While a nose cap 8 is shown, the stent retaining means can be a removable wrap, net or crochet material; or biodegradable material, or bioabsorbable material which over time degrades, releasing the stent.

The deployment device 5 may further include a guide wire (not shown) to assist in placement of the composite prosthesis 14, as known in the art.

FIGS. 2a-2c shows the use of the delivery system 1 of FIG. 1 to deploy prosthesis 14 in a body lumen 12.

FIG. 2a shows the delivery system 1 positioned in the body lumen 12. The outer sheath 6 is retracted with respect to the prosthesis 14 in the direction of the arrow A as shown in FIG. 2b. The retraction of the outer sheath 6 progressively releases the stent 2 along its longitudinal extent and allows the stent 2 to radially expand. The graft 4 which is positioned over stent 2 is also deployed by retraction of outer sheath 6. The graft 4 radially and longitudinally deploys by the radially expanding force of the attached stent 2, and the pressure from the blood flowing, in the directions of the arrows B through the stent open wall structure and into the graft 4 lumen, as shown in FIG. 2b. The nose cap 8 holds the proximal end of the stent 2 so it can be repositioned. It also allows for continuous blood flow during deployment to overcome retrograde pressure.

After deployment of the graft 4 and the major portion of stent 2, the nose cap 8 is advanced away from the stent 2 in the direction of the arrow C as shown in FIG. 2c. This allows stent portion 2a to expand, with the radial expansion of the remainder of the stent 2 the prosthesis 14 is anchored in the body lumen 12.

FIG. 3 and FIGS. 4a-4c show a further embodiment of the invention. The deployment device 25, as shown in FIG. 3, includes the outer sheath 26, an inner sheath 20, and a nose cap 28. The deployment device 25 is prepared to deliver the stent/graft prosthesis 34.

The inner sheath 20 is for overlying the stent/graft prosthesis 34 in a compressed state. The inner sheath 20 is an elongated generally tubular structure which longitudinally surrounds the stent/graft prosthesis 34. The inner sheath is small enough to be inserted within the outer sheath 26 and easily movable therein. The inner sheath 20 can be made of a variety of biocompatible material such as metal, glass or polymeric material; such as nylon, polyurethane, polytetrafluoroethylene (PTFE), expanded polytetrafluoroethylene (ePTFE), fluorinated ethylene, propylene, polyimide, polyether ether ketone, and polybutylene terephthalate or any combinations thereof. The inner sheath 20 can be a thin wall tube, braided, lined, extruded or a sheet formed into a tube.

As shown in FIG. 3, the prosthesis 34 having a stent 22 and graft 24 is placed within the outer sheath 26. Extending portion 22a of the stent 22 is radially compressed within the inner sheath 20 and the nose cap 28. The graft 24 is placed between the outer sheath 26 and the inner sheath 20. A guiding wire (not shown) may be employed to assist with placement of the delivery system 21, as known in the art.

Once the delivery system 21 is in the desired location the outer sheath 26 is retracted, leaving the graft 24 exposed inside the lumen 12, as shown in FIG. 4*a*. The graft 24 begins to radially and longitudinally deploy by the force of the blood flowing, in the direction of arrow B, through the open wall structure of the extending portion 22*a* of stent 22 and through the graft 24, as shown in FIG. 4*a*.

The inner sheath 20 is gradually retracted, liberating stent 22 which was maintained in the compressed state by the inner sheath 20, as shown in FIG. 4*b*. The gradual radial expansion of the stent 22 causes a correlative expansion of the graft 22 until it is pressed against vascular walls, as shown in FIG. 4*b*. During the retraction of the inner sheath 20 the blood flow remains unobstructed, flowing through the open wall structure of the extending portion 22*a* of stent 22 through the graft 24, in direction of the arrows B in FIG. 4*b*. The deployment device 25 may still be repositioned and adjusted, since the prosthesis 34 is not yet completely anchored to the body lumen 12. Once in the desired position the nose cap 8 is removed in the direction of the arrow F as shown in FIG. 4*c*. The extending portion 22*a* of stent 22 radially expands and anchors the prosthesis 34 to the body lumen 12, as shown in FIG. 4*c*.

Yet a further embodiment of the present invention is shown in FIG. 6 and FIGS. 5*a*-5*c*. The delivery system 51, as shown in FIGS. 5*a*-5*c*, delivers multiple stents and/or grafts. The delivery system 51 includes an outer sheath 56, an inner sheath 50, and a nose cap 58 The deployment system 55 is prepared to deliver a stent/graft prosthesis 54.

As shown in FIG. 6, the prosthesis 64 has a first stent 52, a graft 54, and a second stent 60. First stent 52 is an elongated balloon expandable or self-expandable, tubular structure, with a pair of opposing ends and an open wall structure therebetween, as known in the art and above described. First stent 52 is longitudinally shorter than the attached graft 54, defining an extending stent portion 52*a* extending at one end beyond graft 54. While this embodiment is preferred, the first stent 52 may vary in length as the graft 54 having a stent running continuously the within the graft 54.

The graft 54 is an elongated compressible generally tubular structure with a pair of opposing ends and a graft wall therebetween. The graft 54 has an interior graft lumen 80 defined by the graft walls. Any known graft material and structure may be used to form the graft of the present invention. The graft 54 preferably has generally a tubular configuration. The graft 54 may be made from a variety of well known materials in the art and previously discussed.

The graft 54 extends circumferentially about the first stent 52, and the graft 54 is securably attached to the first stent 52, defining the graft attached end 54*a*. The attachment of the graft 54 to the first stent 52 may be accomplished by mechanically securing or bonding the graft 54 to the first stent 52. The attachment of the graft 54 to the first stent 52 may be at one end of the first stent 52 or anywhere between the two ends of the first stent 52. Mechanical securement includes, but is not limited to, the use of sutures, anchoring barbs, textile cuffs and the like. Bonding includes, but is not limited to, chemical bonding, for instance, adhesive bonding, thermal bonding and the like.

The graft 54 extends circumferentially about the second stent 60, and the graft 54 is unattached to the second stent 60. Second stent 60 is an elongated balloon expandable or self-expandable tubular structure, with a pair of opposing ends and a open wall structure therebetween. Second stent 60 may be those known in the art and similar to stent 2 described above. Second stent 60 is unattached to the first stent 52. Second stent 60 is adjacent to one end of first stent 52 and runs continuously in the graft lumen 80 the length of the graft 54. While this is the preferred embodiment, second stent 60 can vary in length and be placed anywhere in the graft lumen 80. For example, the second stent 60 can longitudinally extend beyond the length of the graft 54, or the unattached end 54*b* of the graft 54 can extend beyond the second stent 60.

FIGS. 5*a*-5*c* shows the use of delivery system 51, similar to delivery system 21 of FIG. 3, to deploy prosthesis 64 in a body lumen 12. Delivery system 51 includes a stent/graft prosthesis 64 and a deployment device 55, as shown in FIG. 5*a*. The deployment device 55 includes an outer sheath 56, an inner sheath 50, and a nose cap 58. Second stent 60 is radially compressed and maintained in a compressed state by inner sheath 50. Nose cap 58 maintains the first stent 52 in a radially compressed condition. The graft 54 is maintained in a compressed condition between the outer sheath 56 and the inner sheath 50.

FIG. 5*a* shows the delivery system 51 positioned in the body lumen 12. The outer sheath 56 is retracted exposing graft 54 inside the lumen 12. The blood flows through and around the extending portion 52*a* of first stent 52 open wall structure into the graft 54, in the direction of arrows B, as shown in FIG. 5*a*. The blood flow remains uninterrupted as it flows through and around the extending portion 52*a* of first stent 52 and through graft 54. The nose cap 58 is then removed, allowing the extending portion 52*a* of first stent 52 to radially expand and anchor the prosthesis 64 into the body lumen 12, as shown in FIG. 5*b*. Graft 54 is radially expanded by the force of deployment of stent 52 and blood flow. As shown in FIG. 5*c* the inner sheath 50 is retracted allowing the second stent 60 to radially expand securing graft 54 to the body lumen 12. Another scenario of FIGS. 5*a*-5*c* is the deployment device 55 is used with one continuous stent and the nose cap 58 is removed to allow the extending portion of the stent to anchor the prosthesis and the inner sheath 50 is later retracted to allow the stent to fully deploy. Deploying a stent at the distal end of the graft secures the graft and prevents distal leakage into an aneurysm.

It will be appreciated that the present invention has been described herein with reference to certain preferred or exemplary embodiments. The preferred or exemplary embodiments described herein may be modified, changed, added to or deviated from without departing from the intent, spirit and scope of the present invention. It is intended that all such additions, modifications, amendments and/or deviations be included within the scope of the claims appended hereto.

What is claimed is:

1. A prosthesis delivery system comprising:

a stent/graft composite prosthesis comprising a radially expandable stent having opposed proximal and distal stent ends and a stent body therebetween, and an elongated graft extending from said distal stent end; and a deployment device comprising:

an elongated outer sheath, the outer sheath overlying the graft and said distal stent end of said prosthesis, the outer sheath maintaining said overlayed portions of said prosthesis in a radially compressed state, said outer sheath being retractable with respect to said graft for allowing radial expansion of said graft and said distal stent end; and a stent retaining member, the stent retaining member overlying and engaging said proximal stent end, the stent retaining member maintaining said proximal stent end in a radially compressed state independent of the outer sheath, said proximal stent end is positionable within said stent retaining member, said retaining member being independently removable from said proximal stent end for allowing radial expansion of said proximal stent end independent from the expansion of said distal stent end, wherein said stent retaining member is positionable within said elongated outer sheath and wherein said stent retaining member is retractable in the opposite direction of retraction of said outer sheath.

2. The delivery system according to claim 1, wherein said proximal stent end is defined by a portion of said stent extending outwardly of said outer sheath.

3. The delivery system according to claim 1, wherein said proximal stent end is defined by a portion of said stent extending outwardly of said graft.

4. The delivery system accordingly to claim 1, wherein said outer sheath is a thin wall tube formed of polymeric material.

5. The delivery system according to claim 4, wherein said tube is an extruded tube.

6. The delivery system according to claim 4, wherein said tube is a composite tube.

7. The delivery system according to claim 4, wherein said tube is a sheet formed into a tube.

8. The delivery system according to claim 4, wherein said tube is made form polymeric material which is selected from the group consisting of nylon, polyurethane, polytetrafluorothylene (PTFE), expanded polytetrafluoroethylene (ePTFE), fluorinated ethylene propylene, polyimide, polyether ether ketone, and polybutylene terephthalate or any combination thereof.

9. The delivery system according to claim 1, wherein said stent retaining member is bio-absorbable.

10. The delivery system according to claim 1, wherein the stent is self-expandable.

11. The delivery system according to claim 1, wherein the stent is balloon expandable.

12. A delivery system comprising:
a retaining device, the retaining device comprising a first retaining member and a second retaining member;
a prosthesis, the prosthesis comprising a first end region and a second end region, the first end region being a stent and a second end region being a graft, the prosthesis having a first state and a second state;
in the first state the stent has a reduced diameter and the graft has a reduced diameter wherein the first retaining member surrounds a first portion of the stent and maintains at least the first portion of the stent in the reduced diameter and the second retaining member surrounds a second portion of the stent and the graft and maintains the second portion of the stent and the graft in a reduced diameter; and
in the second state the first portion of the stent has a reduced diameter and the second portion of the stent and the graft have an expanded diameter which is greater than the reduced diameter, wherein the first retaining member surrounds the first portion of the stent and maintains the first portion of the stent in a reduced diameter, the second retaining member does not overlay the prosthesis, and no portion of the second end region of the prosthesis is surrounded by any portion of the retaining device;
wherein the first retaining member is configured to be withdrawn in a first direction and the second retaining member configured is to be withdrawn in a second direction, the first and second directions being opposite directions.

13. The delivery system of claim 12, the prosthesis further having a third state, in the third state, the prosthesis has an expanded diameter wherein neither the first retaining member nor the second retaining member surround the prosthesis.

14. The delivery system of claim 12, wherein the second retaining member is a sheath.

\* \* \* \* \*

UNITED STATES PATENT AND TRADEMARK OFFICE
CERTIFICATE OF CORRECTION

PATENT NO.           : 8,518,096 B2
APPLICATION NO.      : 10/234070
DATED                : August 27, 2013
INVENTOR(S)          : Kristoff Nelson Page 1 of 1

It is certified that error appears in the above-identified patent and that said Letters Patent is hereby corrected as shown below:

In the Claims

Column 9, claim 4, line 14, delete "accordingly" and insert --according--.

Column 9, claim 8, line 23, delete "form" and insert --from--.

Column 10, claim 12, lines 25-30, delete "; wherein the first retaining member is configured to be withdrawn in a first direction and the second retaining member configured is to be withdrawn in a second direction, the first and second directions being opposite directions".

Signed and Sealed this
Twenty-second Day of October, 2013

Teresa Stanek Rea
*Deputy Director of the United States Patent and Trademark Office*